US006977000B2

(12) United States Patent
Vanasse et al.

(10) Patent No.: US 6,977,000 B2
(45) Date of Patent: Dec. 20, 2005

(54) MODULAR TRIAL NECK SEGMENT

(75) Inventors: Thomas M. Vanasse, Thomaston, CT (US); David Robert Tuttle, Memphis, TN (US); Marc Gary Weissman, Warsaw, IN (US)

(73) Assignee: DePuy products, Inc., Warsaw, IN (US)

( * ) Notice: Subject to any disclaimer, the term of this patent is extended or adjusted under 35 U.S.C. 154(b) by 0 days.

(21) Appl. No.: 10/610,460

(22) Filed: Jun. 30, 2003

(65) Prior Publication Data
US 2004/0267372 A1 Dec. 30, 2004

(51) Int. Cl.[7] ............................................... A61F 2/32
(52) U.S. Cl. ................. 623/22.42; 623/22.45
(58) Field of Search ..................... 623/22.12, 22.42, 623/22.43, 22.45, 22.46, 23.21, 19.13, 21.18, 623/22.11, 47, 48, 224.45; 606/89

(56) References Cited

U.S. PATENT DOCUMENTS

| 5,336,268 A | 8/1994 | Rispeter ................... 623/22.4 |
| 5,645,607 A | 7/1997 | Hickey .................... 623/23.35 |
| 5,658,352 A * | 8/1997 | Draenert .................. 623/22.4 |
| 6,193,759 B1 | 2/2001 | Ro et al. ................. 623/23.28 |
| 2003/0088316 A1 | 5/2003 | Ganjianpour | |

* cited by examiner

Primary Examiner—Brian E Pellegrino
(74) Attorney, Agent, or Firm—Maginot Moore & Beck

(57) ABSTRACT

A modular trial neck segment is utilized for trialing a hip prosthesis for a total hip arthroplasty. The modular trial neck segment is preferably, but not necessarily, utilized for trialing a hip prosthesis for a total hip arthroplasty. The trial neck segment includes a mount attachable to a stem or broach, and a neck that is translatable on the mount for providing various neck offsets with respect to the mount and/or broach. Neck offset is changed via movement of the neck in a single plane of motion. This facilitates the use of the subject invention in minimally invasive arthroplasty wherein working dimensions are small. The present design replicates the biomechanics of the neck region of the implant. The mount and slidable neck provide a plurality of neck offsets and/or neck lengths for trialing a final prosthesis in a single device.

12 Claims, 4 Drawing Sheets

MODULAR TRIAL NECK SEGMENT

BACKGROUND

1. Field of the Invention

The present invention relates to prosthetic joints and, more particularly, to a trial neck for a prosthetic joint such as for hip joint replacement.

2. Background Information

Prosthetic joint implants are currently surging in use and technology. In performing most prosthetic joint implants, what is known as a trial or provisional is used before a final prosthesis is used. The trial or provisional is used to select the proper joint prosthesis and/or to orient or align one or more of the components of the final joint prosthesis. The trial or trial components are temporarily implanted to achieve proper sizing, placement and/or orientation of the final joint prosthesis, as well as achieve anatomical orientation of the prosthesis and/or components of the joint prosthesis.

Hip arthroplasty provisionals or trials have a neck that is used to attach a femoral head provisional or trial thereto. The orientation of the neck relative to the shaft of the broach or trial is described in terms of anteversion, neck length, neck angle, and/or neck offset. Because each patient's original femoral neck anatomy is different, the ability to replicate the original femoral neck anatomy of each patient during hip arthroplasty requires multiple neck trials having variations orientations. The use of multiple neck segments is not advantageous since it requires more time, increased instrument cost and increased space in the instrument sterilization case Thus, trialing systems utilized by many hip implants or prostheses generally consist of a broach and a neck segment. In order to intraoperatively change the offset of the trial (i.e. neck segment and broach), the neck trial must be removed and another neck trial must be put in its place. Thus, multiple neck trials that are exchangeable with one another relative to the broach are necessary in order replicate the original hip anatomy.

Other hip systems utilize only one neck segment with the offset incorporated into the location of the trunion of the broach. This design, however, does not mimic the exact geometry of the actual implant. While it is desired to be able to try several neck offsets relative to the broach in order to achieve a proper head positioning for the final implant, the prior art is deficient.

In U.S. Pat. No. 5,645,607 issued to Hickey, a hip trial or prosthesis having an adjustable neck portion is disclosed in which the problem of multiple neck trials is addressed. The adjustable neck of Hickey allows the trialing of various neck offsets in order to achieve a correspondence between the spatial orientation of a patient's original anatomy and a final implanted hip ball prosthesis.

However, Hickey requires a vertical height change of the neck segment in order to move between the various offsets. Where vertical height is restricted during surgery, especially in current, less invasive arthroplasty procedures, vertical height adjustment is undesireable.

It should be appreciated in view of the above, that it is desired to have a single trial neck for a trial prosthesis that provides a plurality of offsets.

It should be appreciated in view of the above, that it is further desired to have a single trial neck for a trial prosthesis that is usable in minimally invasive implant procedures.

It should also be appreciated in view of the above, that it is still further desired to have a single trial neck for a trial prosthesis that requires only one direction of movement to affect translation of the trial neck into a plurality of offsets.

SUMMARY

The subject invention is a modular neck segment for a hip prosthesis or hip prosthesis trial. The modular trial neck segment is preferably, but not necessarily, utilized for trialing a hip prosthesis for a total hip arthroplasty. The trial neck segment includes a mount attachable to a stem or broach, and a neck that is translatable on the mount for providing various neck offsets with respect to the mount and/or broach. Neck offset is changed via movement of the neck in a single plane of motion without a change in neck height. This facilitates the use of the subject invention in minimally invasive arthroplasty wherein working dimensions are small.

One portion of a retention mechanism is provided in the mount that mates with another portion of the retention mechanism of the trail broach to situate the mount onto the broach. The mount includes a collar and lateral tapered geometry of a typical neck segment. The neck segment is temporarily retained on the mount for replicating various neck offsets or locations relative to the mount and/or broach. The present design replicates the biomechanics of the neck region of the implant.

In one form, the subject invention is a neck for a hip trial for a hip implant. The neck includes a mount and a stem slidably retained on the mount. The stem is translatable relative to the mount using a single plane of motion to affect a plurality of neck offsets without effecting a change in neck height.

BRIEF DESCRIPTION OF THE DRAWINGS

In the drawings.

Corresponding reference characters indicate corresponding parts throughout the several views. Like reference characters tend to indicate like parts throughout the several views.

DESCRIPTION OF THE PREFERRED EMBODIMENT(S)

Figure 1:
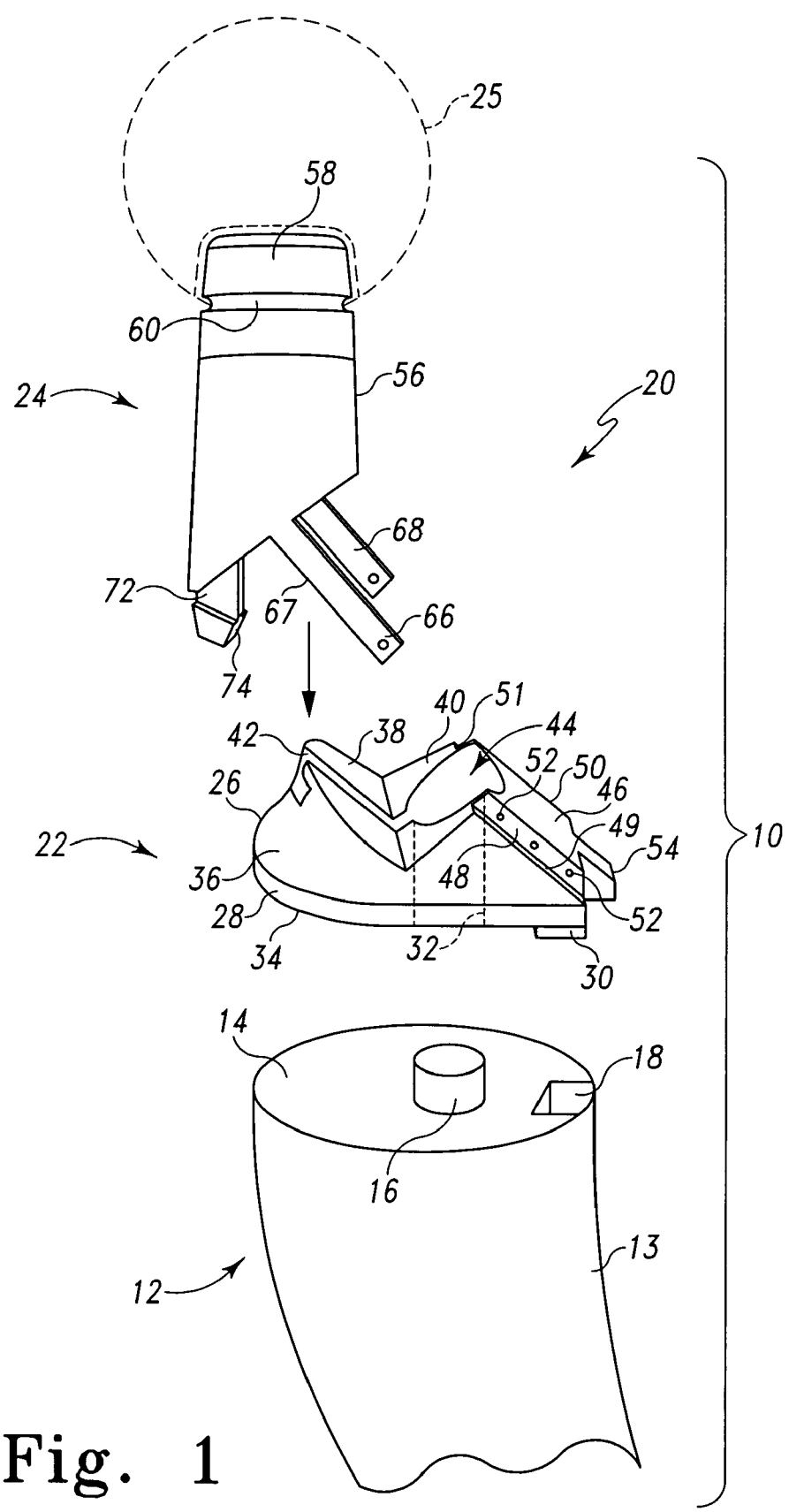
FIG. 1 is an exploded perspective view of a hip provisional or prosthesis having a modular trial neck in accordance with the principles of the subject invention.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention.

Referring now to FIG. 1 there is shown an exemplary hip trial, generally designated 10, for trialing a hip implant or prosthesis. The hip trial 10 includes a broach, stem, stem trial or the like 12 and a modular neck, neck portion, neck segment or the like 20 in accordance with the principles of the subject invention. A femoral head 25 is utilized with the hip trial 10 as connected to the modular neck segment 20. The femoral head 25 is connectable to the neck 20 in a typical manner.

The broach 12 includes an elongated body 13 defining a longitudinal axis and having an upper surface 14 at one end thereof. The remaining portion of the broach 12 is not shown, but is typical of an implantable broach. The upper surface 14 is preferably, but not necessarily, flat and defines a plane that is offset from normal relative to the longitudinal axis. A knob, boss, protrusion, convexity or the like 16 extends from the upper surface 14. While the boss 16 is shown as cylindrical, it should be appreciated that the boss 16 may take other shapes. Formed or disposed in the upper surface 14 at one side of the body 13 is a notch, cutout, concavity or the like 18. The notch 18 functions to aid in rotatably fixing the modular neck segment 20 on the broach 12. While shown as a rectangle, the notch 18 may take any appropriate configuration. This includes the provision of temporary locking means. Particularly, the notch 18 forms one portion of a two portions cooperating to constrain the neck segment 20 from rotation relative to the broach 12.

The neck segment 20 of the trial 10 includes a mount, base or the like 22 and a neck portion 24. The mount 22 is received on the broach 12. Particularly, the mount 22 has a bore, hole, concavity or the like 32 that is sized and/or configured to receive the boss 16 thereby forming a trunnion. The bore 32 is preferably, but not necessarily, configured in a generally complementary manner as the boss 16 and thus may take other shapes according to the shape of the boss 16.

The mount 22 is defined by a body 26 that is fashioned from a material typical for trials such as metal, plastic, ceramic, composite or the like. The body 26 has a collar or lower portion 28 from which depends a protrusion, ledge, flange, tab or the like 30. The flange 30 is preferably, but not necessarily, configured in a generally complementary manner as the notch 18 and thus may take other forms according to the shape of the notch 18. When the mount 22 is situated on the broach 12, and the boss 16 is received in the bore 32, a bottom surface 34 of the body 26 abuts the upper surface 14. Moreover, the flange 30 is received in the notch 18. This temporarily, non-rotatably seats the neck segment 20 (i.e. the mount 22 thereof) onto the broach 12.

It should be appreciated that the broach 12 depicted in FIG. 1 is not necessarily accurate with respect to the natural curvature of the broach 12 and thus the orientation of the surface 14 with respect to the bone in which it is implanted or the socket to which it faces. Particularly, the surface 14 is angled toward the socket of the joint as is typical of hip implants. Thus, the orientation of the neck segment 20 is not necessarily as shown. The orientation of the neck segment is as that shown in FIGS. 5, 6 and 7. Moreover, the various components of the broach 12 (e.g. the boss 16 and/or the notch 18) may be in different locations on the surface 14. It should be appreciated that the illustration of FIG. 1 is only exemplary of the neck segment 20 and not necessarily of the relationship of the neck segment 20 to the broach 12 and/or the patient's anatomy.

Figure 2:
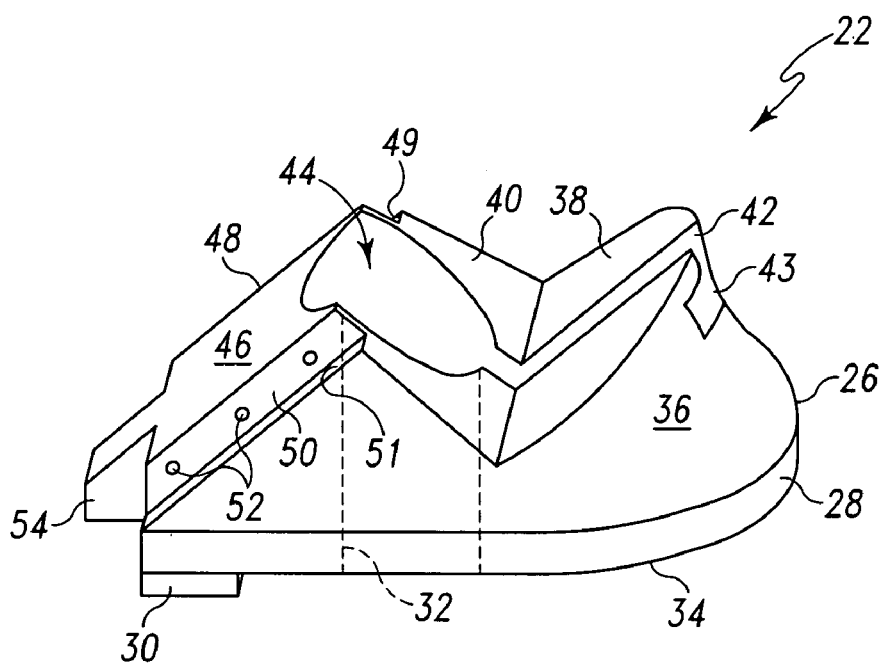
FIG. 2 is an enlarged perspective view of a mount portion of the modular trial neck of FIG. 1.

Referring additionally to FIG. 2, the body 26 of the mount 22 has an ovoid shaped sidewall 36 (in cross-section) that extends generally upwardly from the collar 28. The sidewall 36 is tapered inwardly as it extends upwardly. This simulates the typical final prosthesis neck configuration. The neck segment 20 maintains the taper regardless of the neck offset, position or height. An oblique cutout in the body 26 defines a first surface 38 and a second surface 40. The surface 38 provides a guide or seating surface for the neck portion 24 and is preferably angled, slanted or sloped. The second surface 40 is also slanted, sloped or angled. A configured slot, channel, groove or the like 42 is disposed in the body 26 extending from and along the surface 38. A bore 44 is disposed in the opposite surface 40.

The body 26 further has a protruding front sloping or slanted surface 46 that defines two side surfaces 48 and 50, and which terminates in a nose or front portion 54. The side surfaces 48 and 50 are essentially parallel to one another and perpendicular or normal to the surface 46. Each side surface 48, 50 has a plurality of holes, protrusions or the like 52 (preferably, but not necessarily, and hereinafter, holes). The holes 52 are distributed along the side thereof, with each side 48 and 50 having the same pattern forming pairs of holes 52 on opposite sides of the surface 46. The holes form one part of a releasable retaining or retention mechanism or the like for the neck portion 24. The side surfaces 48, 50 connect to a respective ledges or rails 49, 51 that are preferably, but not necessarily, perpendicular or normal to its respective side surface. The ledges 49, 51 provide seating and/or sliding surfaces for a portion of the neck portion 24.

The neck segment 20 is operative, configured and/or adapted to provide a plurality of neck offsets with respect to the broach 12 through cooperation of the neck portion 24 on the mount 22. Particularly, the neck portion 24 is translatable on the stationary mount 22 such that various offsets of the neck portion 24 relative to stem 12 are achieved. In accordance with an aspect of the subject invention, translation or movement of the neck portion 24 on the mount is accomplished in one plane of motion wherein neck height is not changed. Thus, neck offset is achieved by moving the neck portion in one direction (horizontal) only. In the present embodiment, while the plane of motion 38 appears to be slanted, sloped or angled, the plane of motion (surface 38) is essentially normal to a longitudinal axis of the broach 12 or bone in which the broach 12 is implanted when the neck segment 20 is situated thereon. Again, this is particularly shown in FIGS. 5–7 and discussed below.

Figure 3:
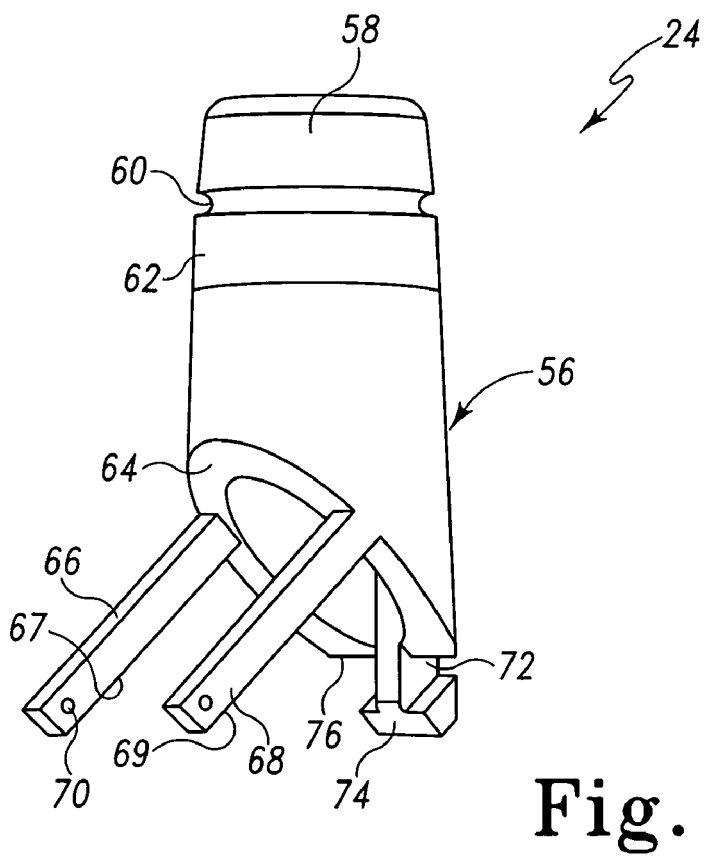
FIG. 3 is an enlarged perspective view of a neck portion of the modular trial neck of FIG. 1.

Referring additionally to FIG. 3, the neck or neck portion 24 of the neck segment 20 is shown in greater detail. The neck 24 is defined by a body 56 that is generally cylindrical in shape, but may be formed as other shapes. The body 56 has a tapered top 58 and an annular groove 60 to receive a femoral component 25 (see FIG. 1). Various sizes and of femoral components 25 may be placed on the neck 24 for selection of an appropriate size for the patient.

A lower portion 62 of the body 56 terminates in a slanted bottom surface 64 that radially dissects the cylinder at an angle away from vertical (an axis thereof). The body 56 carries two arms 66 and 68 that outwardly extend at an angle from the slanted surface 64. The arm 66 defines a bottom surface 67 and has a hole or knob 70 at an inside side at the end thereof. The arm 68 defines a bottom surface 69 and has hole or knob 70 (not seen) at an inside side at the end thereof. The knobs 70 form an oppositely disposed pair of knobs that form a second portion of the temporary retaining or retention feature of the subject invention along with the holes 50 (the first portion).

The body 56 also includes a flange 72 that axially depends from a side of the slanted surface 64 at a bottom portion 76 thereof. The flange 72 terminates in a slanted T section 74. The configuration of the T section 74 is configured in like manner to the configured slot 42 of the mount 22, and is thus adapted to be received in the slot 42. As such, the flange 72 is of sufficient length to extend into the slot 42 when the neck 24 is situated on the mount 22.

Figure 4:
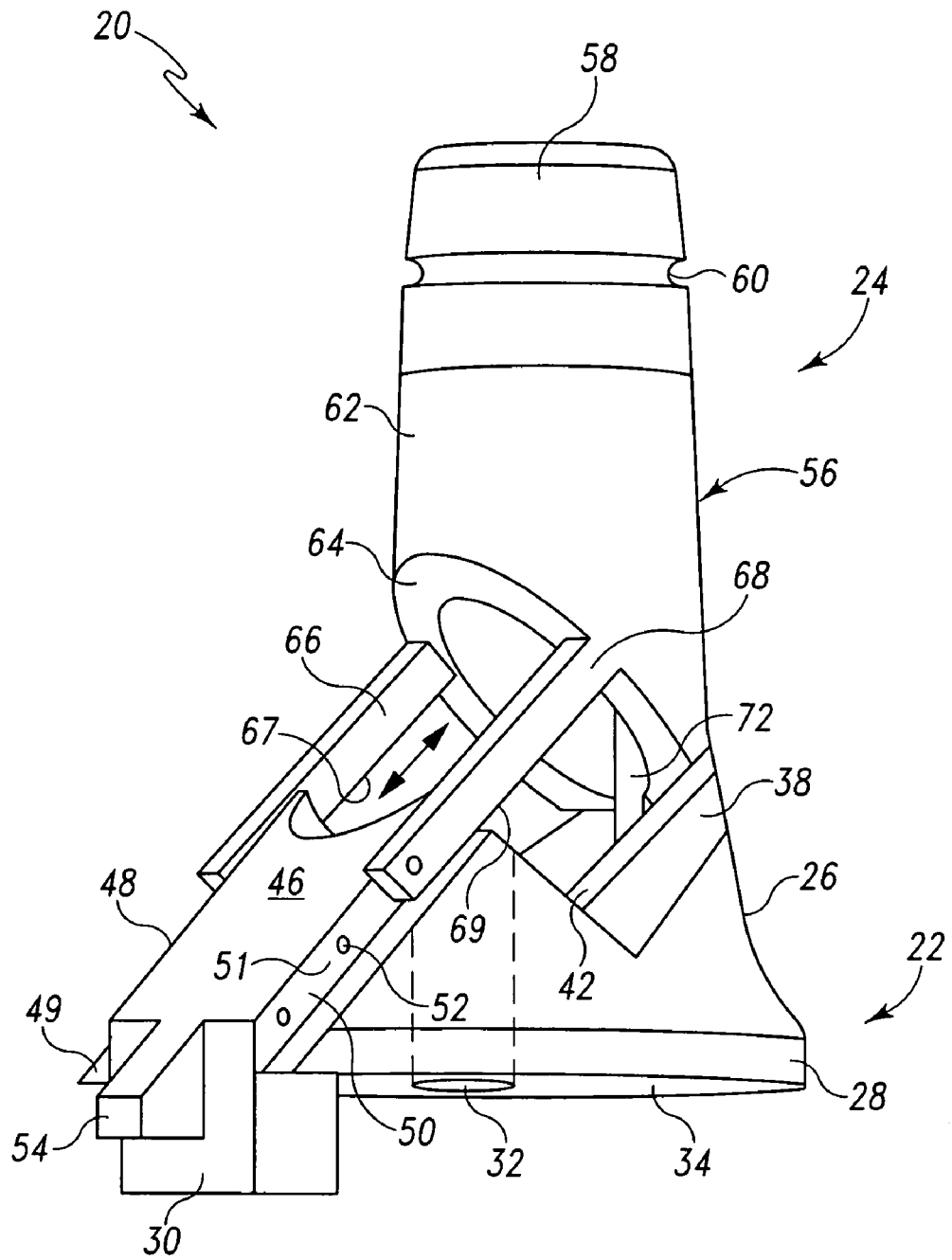
FIG. 4 is an enlarged perspective view of the modular trial neck of FIG. 1.

Referring to FIG. 4, the neck segment 20 alone is shown in an assembled state in order to illustrate the manner in which the neck portion 24 is received on the mount 22. The neck portion 24 is shown in one of a plurality of positions or offsets that is achievable with the neck segment 20. The flange 72 and thus the T section 74 that depends therefrom, is slidably received in the slot 42 of the mount 22. This situates the bottom portion 76 of the slanted surface 64 of the body 56 onto the sloped surface 38 of the mount 22. At the same time, the arms 66 and 68 are seated on respective rails 49 and 51 abutting the sides 48 and 50 respectively. The arms are preferably resilient to allow limited deformation (e.g. bending) but spring back after bending.

The arms 66, 68 are also slightly undersized with respect to the width between the arms and the width of the surface 46. The knobs 70 of the arms 66, 68 (of which the knob of the arm 68 cannot be seen in FIG. 4) thus fit into opposite holes 52 (hole pair) of the sides 48 and 50 to fix the neck 24 in a particular position along the mount 22. This creates a particular offset of the neck 24. The slant of the surface 38 and the slant of the surface 46 are preferably, substantially the same, but not necessarily. The top 58 of the body 56 is also at a particular height relative to the bottom surface 34 of the mount 22 (which can be equated with the surface 14 of the stem 12). The portion 62 is constrained from axial movement relative to the slopping surface 38. The sloping surface 38 is, however, essentially horizontal when situated on the broach 12.

The body 56 thus moves or translates in only the X coordinate direction (horizontal) such that the neck height remains the same regardless of the offset position. Thus, as the neck 24 moves relative to the mount 22, the body 56 is constrained by cooperation of the flange 72 and slot 42 to move horizontally with respect to the mount 22. The arms 66, 68 move along the slope of the rails 49, 51 of the surface 46. While the flange 72 is free to move along the slot 42 unhindered, the knobs 70 of the inwardly biased arms 66, 68, lock into each pair of holes 52. The hole pairs thus define the number of discrete neck offsets.

Figure 5:
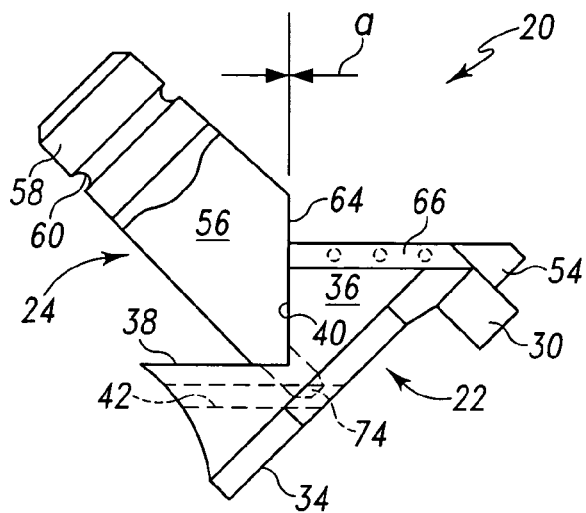
FIG. 5 is a side view of the modular trial neck illustrating one position of the neck portion with respect to the mount portion thereof.
Figure 6:
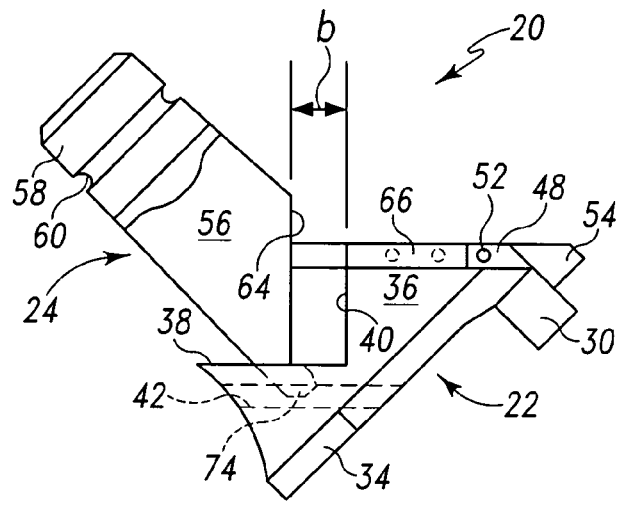
FIG. 6 is a side view of the modular trial neck illustrating another position of the neck portion with respect to the mount portion thereof.
Figure 7:
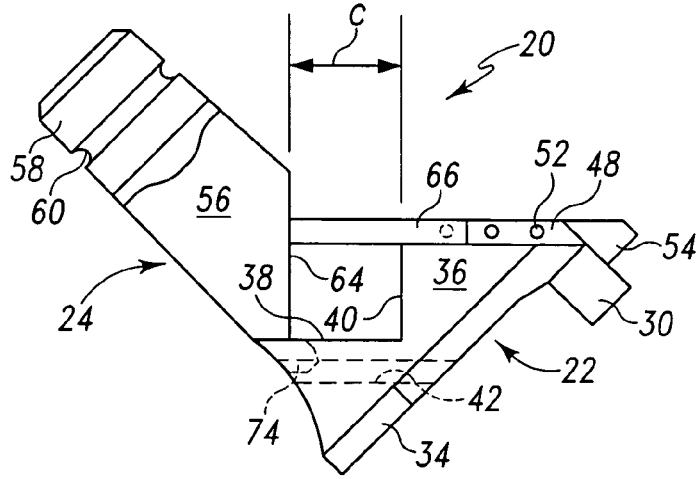
FIG. 7 is a side view of the modular trial neck illustrating another position of the neck portion with respect to the mount portion thereof.

Movement of the neck 24 relative to the mount 22 is particularly shown in FIGS. 5–7 and reference is now made thereto in conjunction with the following description thereof. Particularly, FIGS. 5, 6 and 7 show a progression from a first position (FIG. 5), through a second position (FIG. 6) and to a third and final or last position (FIG. 7). The number and spacing of positions between the first position and the last position is arbitrary (here the number of between positions is one position). Additionally, the neck portion 24 may be initially seated at any of the positions. Moreover, the description of the progression from a bottom or first position to a top or final position is also arbitrary. Even further, it should be appreciated that the orientation of the neck segment 20 is as it is when situated on a broach 12.

In FIG. 5, the neck portion 24 is at an initial or zero (0) mm offset (i.e. the slanted surface 64 of the neck portion 24 is seated against the surface 40 of the mount 22) which is represented by the dimension "a". The T portion 74 of the flange 72 is bottomed out in the slot 42. The arms 66, 68 are fully extended along the rails 49, 51 such that the knobs 70 are seated in the lowermost hole pair 50. The body 56 extends a vertical distance from the surface 38 of the mount 22. The position of FIG. 5 corresponds to a first offset position of the neck on the mount.

In FIG. 6, the neck 24 has been horizontally moved into a second position, providing another offset of the neck. The body 56 has moved along the surface 38 during translation thereof on the mount 22, i.e. during its travel from the position of FIG. 5 to the position of FIG. 6. The T flange 74 slides within the channel 42 as the bottom of the arcuate section 64 rides on the slanted surface 38. The arms 66, 68 move along the respective rail 49, 51 such that the knobs 77 thereof are retained in the second set or pair of holes 52.

The body 56 extends the same vertical distance from the surface 38 of the mount 22 as in the other positions. Thus, it can be appreciated that the neck segment 20 provides horizontal translation without vertical translation. Moreover, horizontal translation is the only translation and may be considered as motion in a single plane. The length of the offset is labeled "b" and is approximately 5.5 mm long along an X-axis or a horizontal. The height of the neck 24 remains the same as the position of FIG. 5. Thus, offset of the neck 24 is accomplished or achieve by translation of the neck in a single direction or plane of movement. The resilient arms 66, 68 and the cooperation of the knobs 70 with the holes 52 provide temporary retention of the neck 24 relative to and on the mount 22.

In FIG. 7, the neck 24 has been moved into a final position, providing another offset of the neck. The body 56 has moved in the horizontal direction during its translation on the mount 22, i.e. during its travel from the position of FIG. 6 and the position of FIG. 7. The T flange 74 slides within the channel 42 as the bottom of the arcuate section 64 rides on the slanted surface 38. The arms 66, 68 move along the respective rail 49, 51 such that the knobs 77 thereof are retained in the last set or pair of holes 52.

The body 56 again extends the same vertical distance from the bottom surface 34 of the mount 22. The dimension labeled "c" corresponds to a middle position of the neck on the mount. The neck 24 is shifted horizontally (X-axis or vertical Y). The combined height and medial to lateral translation of the neck 24 relative to the mount 22 provides another offset of the neck. The vertical distance or height of the neck 24, however, is now greater than the vertical height of the neck when in the positions of FIGS. 5 and 6.

There is a plurality of advantages of the subject invention arising from the various features of the subject invention described herein. It will be noted that further alternative embodiments of the subject invention may not include all of the features described yet still benefit from at least some of the advantages of such features. Those of ordinary skill in the art may readily devise their own implementations of the subject invention that incorporate one or more of the features of the subject invention and that fall within the spirit and scope of the subject invention.

What is claimed is:

1. A neck segment for a prosthesis trial, the neck segment comprising:
   a mount adapted to be temporarily received on a prosthesis stem, said mount having an adjustment surface and a slot formed in said adjustment surface; and
   a neck adapter to temporarily receive a femoral head and having a flange configured to be slidably received in said slot,
   wherein said neck is translatable along said adjustment surface utilizing only a single plane of motion whereby a plurality of neck offsets are achieved, wherein said mount includes a first portion of a temporary retention mechanism, and said neck includes a second portion of said temporary retention mechanism, wherein said neck portion comprises at least one arm; and wherein said retention mechanism comprises one of a knob and a hole associated with said at least one arm, and another one of a knob and a hole associated with the mount.

2. The neck segment of claim 1, wherein said neck is translatable along said mount utilizing only a single plane of motion whereby said single plane of motion is horizontal.

3. The neck segment of claim 1, wherein said at least one arm is resiliently biased inwardly to effect retention of said neck via said retention mechanism.

4. The neck segment of claim 1, wherein said neck is configured to releasably receive a femoral component thereon.

5. A prosthetic trial comprising:

a trial broach; and a trial neck non-rotatably seatable on the trial broach, said trial neck comprising:
   a mount adapted to be temporarily received on said trial broach, said mount having an adjustment surface, a slot formed in said adjustment surface, and a first portion of a temporary retention mechanism; and
   a neck adapted to temporarily receive a femoral head, said neck having a flange configured to be slidably received in said slot, and a second portion of said temporary retention mechanism;

wherein said neck is translatable along said adjustment surface utilizing only a single plane of motion whereby a plurality of neck offsets are achieved, wherein said neck comprises at least one arm; and wherein said retention mechanism comprises one of a knob and a hole associated with said at least one arm, and another one of a knob and a hole associated with the mount.

6. The prosthesis trial of claim 5, wherein said neck is translatable along said mount utilizing only a single plane of motion whereby said single plane of motion is horizontal.

7. The prosthesis trial of claim 5, wherein said at least one arm is resiliently biased inwardly to effect retention of said neck via said retention mechanism.

8. The prosthesis trial of claim 5, wherein said neck is configured to releasably receive a femoral component thereon.

9. A modular trial neck for a hip prosthesis trial comprising:

a base adapted to be non-rotatably mounted on a trial broach; and a neck slidably carried by said base and providing a plurality of neck offsets relative to said base by movement of said neck relative to said base in a single plane of motion only, wherein said base has an adjustment surface upon which said neck slides, a slot formed in said adjustment surface, and a first portion of a temporary retention mechanism, and said neck has a flange configured to be slidably received in said slot and a second portion of said temporary retention mechanism, wherein said neck comprises at least one arm; and wherein said retention mechanism comprises one of a knob and a hole associated with said at least one arm, and another one of a knob and a hole associated with the mount.

10. The modular trial neck of claim 9, wherein said single plane of motion is horizontal.

11. The modular trial neck of claim 9, wherein said at least one arm is resiliently biased inwardly to effect retention of said neck via said retention mechanism.

12. The modular trial neck of claim 9, wherein said neck is configured to releasably receive a femoral component thereon.

* * * * *